United States Patent [19]

Elton

[11] Patent Number: 5,160,790
[45] Date of Patent: Nov. 3, 1992

[54] LUBRICIOUS HYDROGEL COATINGS

[75] Inventor: Richard K. Elton, Glens Falls, N.Y.

[73] Assignee: C. R. Bard, Inc., Glens Falls, N.Y.

[21] Appl. No.: 607,550

[22] Filed: Nov. 1, 1990

[51] Int. Cl.$^5$ .................... B32B 27/34; B32B 27/36; B32B 27/40

[52] U.S. Cl. .................. 428/412; 428/423.1; 428/423.3; 428/423.5; 428/423.7; 428/423.9; 428/424.8; 525/123

[58] Field of Search ............... 428/423.1, 423.3, 423.5, 428/423.7, 424.8, 423.9, 412; 525/123

[56] References Cited

U.S. PATENT DOCUMENTS

| | | | |
|---|---|---|---|
| 4,027,676 | 6/1977 | Mattei | 128/335.5 |
| 4,087,567 | 5/1978 | Sullivan | 427/2 |
| 4,100,309 | 7/1978 | Micklus et al. | 427/2 |
| 4,119,094 | 10/1978 | Micklus et al. | 428/420 |
| 4,156,067 | 5/1979 | Gould | 528/73 |
| 4,192,827 | 3/1980 | Mueller et al. | 525/123 |
| 4,229,551 | 10/1980 | Straub | 525/337 |
| 4,255,550 | 3/1981 | Gould | 528/44 |
| 4,373,009 | 8/1983 | Winn | 428/424.2 |
| 4,459,317 | 7/1984 | Lambert | 428/423.1 |
| 4,467,073 | 8/1984 | Creasy | 525/127 |
| 4,487,808 | 12/1984 | Lambert | 428/423.1 |
| 4,585,666 | 4/1986 | Lambert | 427/2 |
| 4,589,873 | 5/1986 | Schwartz et al. | 604/265 |
| 4,642,267 | 2/1987 | Creasy et al. | 428/413 |
| 4,666,437 | 5/1987 | Lambert | 604/265 |
| 4,705,709 | 11/1987 | Vailancourt | 428/36 |
| 4,729,914 | 3/1988 | Kliment et al. | 428/36 |
| 4,743,673 | 5/1988 | Johnston | 528/60 |
| 4,769,013 | 9/1988 | Lorenz et al. | 604/265 |
| 4,835,003 | 5/1989 | Becker et al. | 427/2 |

Primary Examiner—Paul J. Thibodeau
Assistant Examiner—D. S. Nakarani
Attorney, Agent, or Firm—Morgan & Finnegan

[57] ABSTRACT

A flexible, lubricious organic coating is formed by applying a mixture of an isocyanate, a polyol, polyvinylpyrrolidone (PVP), and carrier liquid to a surface to be coated. The carrier liquid is removed and the mixture reacted to form a lubricious, flexible coating, particularly suitable for use as a protective lubricious coating on medical devices introduced into the body. The coating exhibits a significantly reduced coefficient of friction when exposed to water or aqueous solutions.

16 Claims, No Drawings

LUBRICIOUS HYDROGEL COATINGS

BACKGROUND OF THE INVENTION

It has long been known that hydrophilic coatings with low friction (coefficient of friction of 0.3 or less) are useful for a variety of medical devices such as catheters, catheter introducers and the like. When low friction surfaces are used, the devices, upon introduction into the body, slide easily with arteries, veins, cannula and other body orifices and passageways. There have been a wide variety of methods used to provide the surfaces desired. In some cases the material of the catheter or medical device is formed of a material having good anti-friction properties such as poly(tetrafluoroethylene) or other plastics which tend to avoid abrasion with the body. However, in many cases the selection of materials does not provide the anti-slip properties desired in conjunction with other desirable properties for the particular medical device.

The art has recognized that polymer surfaces can be provided with hydrophilic coatings formed from combinations of isocyanate, polyurethane and polyvinylpyrrolidone (PVP).

For example, U.S. Pat. No. 4,642,267 discloses a coating which is a simple blend of thermoplastic polyurethane and PVP. When deposited on a substrate and dried, no reactions occur. The coating does not bond to the plastic substrate, and can readily be redissolved in a solvent. Furthermore, the PVP is only lightly complexed, thus allowing the coatings to become generally soft and readily removed when wet.

The present invention, in contrast, is a crosslinked system, and thus more tightly complexes the PVP. Furthermore, some reaction may occur between the isocyanate and the substrate to improve adhesion.

The prior art coatings using PVP typically rely on a 2 step, 2 coating process, usually involving a primer coat of isocyanate or isocyanate/polymer blend which is dried, followed by a second coat containing PVP, a blend of PVP and another polymer, or another hydrophilic polymer such as poly(ethylene oxide). The 2 coatings, one superimposed on the other, are then baked to effect a cure. Several disadvantages to this process exist:

1. The exact ratio of primer material to PVP is difficult to control, as it relies on whatever amounts of primer and PVP happen to be deposited by the wet film during the respective dip coating steps.
2. The primer may begin to redissolve in the second coating solution, causing some loss of primer, and further resulting in difficulty in controlling the primer/PVP ratio.
3. Additional facilities and time are needed for coating with a 2 step process, as compared to a 1 step process.

Prior patents have suggested applying solutions of polyvinylpyrrolidone with isocyanate and/or polyurethane in multi-step operations. These coatings often lack good durability. For example, U.S. Pat. No. 4,585,666 to Lambert discloses medical devices having hydrophilic coatings formed from an isocyanate layer overcoated with a polyvinylpyrrolidone layer. However, such coatings are of polyurea materials formed from a first solution of an isocyanate being applied to a base, the solvent then evaporated, followed by a second solution application of a polyvinylpyrrolidone, in turn followed by evaporation of the solvent. Cure is effected by baking, in the presence of moisture, thus producing a polyurea. This type of application provides polyurea materials which do not have the tenacity of the coatings of the present invention. Additionally, the multistep procedure makes it difficult to tailor properties and values of the final coatings.

In my copending application Ser. No. 512,872, filed Apr. 23, 1990, there are disclosed coatings which are the result of polyurethane linkages in combination with an association of poly(ethylene oxide). Such poly(ethylene oxide) containing coatings are formed using a one-dip process to provide low friction coatings which are abrasion resistant in the body, hydrophilic and lubricious.

SUMMARY OF THE INVENTION

It is an object of this invention to provide a hydrophilic, extremely lubricious organic coating which exhibits a significantly reduced coefficient of friction when exposed to water or aqueous solutions.

It is the object of this invention to provide a hydrophilic, extremely lubricious organic coating which has good adherence to substrates, particularly plastic substrates.

It is another object of this invention to provide a hydrophilic, extremely lubricious organic coating which retains its lubricity when wet even after prolonged contact to water or aqueous solutions, and even after repeated moistening/drying cycles.

It is another object of this invention to provide coatings in accordance with the preceding objects which are particularly useful for application to outer plastic surfaces of medical devices with good adherence to the devices and which are non-toxic and non-deleterious to the body.

It is a further object of this invention to control the final composition by formulating the coating solution using known and desired quantities of the isocyanate, PVP and polyol components.

Another object of this invention is to provide a method of applying a hydrophilic, extremely lubricious organic coating as in the preceding objects, which method can be carried out using a single coating solution which has an enhanced useful lifetime or pot life and which is efficacious by minimizing manufacturing costs accompanying the use of conventional equipment.

A still further object of this invention is to provide a method in accordance with the preceding objects which provides a flexible urethane coating having a high molecular weight polyvinylpyrrolidone (PVP) associated therewith and which is adherent to underlying substrates of varying organic polymeric materials.

According to the present invention a hydrophilic, highly lubricious, organic coating is formed from the reaction, on a surface to be coated, of a mixture containing an isocyanate, a polyol and a polyvinylpyrrolidone (PVP) in a carrier liquid. A urethane coating is formed having good adherence to the substrate and good anti-friction properties. The coating can be formed on various medical devices including catheters and catheter medical tubing.

More particularly, the present invention relates to a hydrophilic polymer network, useful as a coating for certain medical devices, which exhibits a significantly reduced coefficient of friction when exposed to water or aqueous solutions.

Such a system contains 4 major components:

1. A high molecular weight polyvinylpyrrolidone (PVP), or a blend of two or more such PVP products.
2. A polyhydroxy species or polyol containing at least 2 hydroxyl groups per molecule, or a blend of two or more such polyols.
3. An isocyanate prepolymer or monomer containing at least 2 NCO groups per molecule, or a blend of two or more such isocyanates.
4. A solvent or blend of solvents suitable for dissolving components 1-3, which does not significantly react with the components.

The coating of this invention permits a stoichiometric reaction to occur between the isocyanate and the polyol to produce a crosslinked polyurethane network in the intimate presence of the polyvinylpyrrolidone. The isocyanate/polyol reaction produces a polyurethane which is believed to complex the polyvinylpyrrolidone by hydrogen bonding, most likely between the carbonyl oxygen of the PVP and the NH hydrogen of the urethane linkage.

According to the method of this invention, a coating as defined above is formed by applying a solution of the mixture and carrier liquid to the substrate by conventional coating methods, including spraying, dipping, painting and the like. The application step is followed by drying to remove the carrier liquid either by evaporating the solvent at room temperature or by heating. In a subsequent step, the coating formed is cured at room temperature or with heating to form a polyurethane network having PVP entrapped therein.

The disadvantages of prior art procedures using a two step process are overcome by the present invention which involves a one step process, thus permitting a single coating solution of controllable composition. Further advantages of employing a one step process are as follows:

1. The present coatings can be formulated over a wide range of properties such as lubricity, durability, adhesion to various surfaces, etc., because the exact composition of the polyurethane -PVP complex can be tailored to the desired result, and particular substrate and end-use application by selecting the specific isocyanate and polyol combination from a wide range of products available commercially.
2. The ratio of polyurethane (total mass of isocyanate plus polyol) to PVP can be varied exactly during preparation of the coating solution.

More particularly, in the coating of this invention, the PVP becomes entrapped by entanglement in the developing polyurethane network and is evenly distributed throughout the coating. The strong complexing between PVP and crosslinked polyurethane prevents PVP from leaching out of the film when it is exposed to water. On contact with water, the film imbibes a significant amount of water and swells to produce a very hydrophilic gel. The gel is stable in water and does not dissolve even after prolonged exposure of up to several weeks duration. The surface of an article coated with this film becomes very lubricious, since the wet gel is capable of associating a significant quantity of water and thus maintaining a fluid layer between the coated surface and another surface moving with respect to it.

It is a feature of this invention that the coating will imbibe water and become lubricious upon exposure to water or aqueous fluids as within the body. The coating can be wetted before introduction into the body. Because it is a cross-linked system resulting from a curing operation, the coating will remain firmly bonded to a substrate even when hydrated. The coating can be dried and remoistened repeatedly while retaining its lubricating properties. The lubricity of the wet coating is retained indefinitely, even after repeated moistening/drying cycles. Coatings thus prepared retain properties when exposed to normal gamma ray sterilization doses or when sterilized with ethylene oxide. These coatings do not appear to lose significant weight on prolonged exposure to water. Furthermore, the composition of the coating system is essentially uniform, and therefore any reasonable coating thickness can be achieved simply by varying the solids content.

While the exact mechanism is not definitely known, as pointed out earlier, it appears that the polyol and isocyanate react to form a cross-linked matrix or network of polyurethane which strongly complexes the polyvinylpyrrolidone by hydrogen bonding so that it becomes an integral part of the polyurethane coating.

The coatings of this invention are particularly suitable to application on plastic surfaces, such as polyurethane or nylon, because some of the isocyanate in the coating mixture can react with active sites on the plastic substrate to provide good bonding of the coating.

DESCRIPTION OF PREFERRED EMBODIMENTS

A highly lubricious coating is formed overlying a catheter body formed of a flexible organic polymeric material. The coating is formed from a mixture containing an isocyanate, a polyol and polyvinylpyrrolidone in a carrier liquid.

In addition, the mixture can contain additives to alter the characteristics of the coatings in substantially known manners. For example, conventional additives include antioxidants, flow control agents, and air release agents.

The ratio of weight of the polyurethane formed in situ to PVP varies from 0.05 to 3.0 and is preferably from 0.20 to 1.0. The stoichiometric ratio of total NCO groups in the isocyanate to total OH groups in the polyol can vary from 0.75 to 3.0 and is preferably from 1.0 to 1.5. Generally, in producing a polyurethane of controllable composition, it is preferable to use an NCO to OH ratio close to 1.0. However, a preferred ratio is usually somewhat greater than 1.0, since it is known that isocyanates readily react with water, and that incidental quantities of water can integrate with the uncured coating. This water is present from various sources such as atmospheric moisture, moisture in solvent, or moisture associated with the polyvinylpyrrolidone.

The isocyanate species must contain at least two NCO groups per molecule, and the polyol must contain at least two OH groups per molecule. In order to form a crosslinked polyurethane network, the sum of the average NCO functionality and average OH functionality must exceed 4. It is preferable to use an isocyanate with an NCO functionality of 2, and a polyol with a functionality of 3, 4 or higher. However, use of an isocyanate with an NCO functionality greater than 2 with a polyol of OH functionality of 2 is suitable.

The coating mixture, in solution, is prepared by weighing the appropriate quantities of isocyanate, polyol and polyvinylpyrrolidone stock solution and adding them into an appropriate mix vessel. Additional solvents can be added to adjust the viscosity and solids content. Solids contents may be in a range of from 0.4 to 15% (w/w), with 1.5 to 4% (w/w) preferred, depending on the solvent used and other considerations. This solution is mixed well and then applied to an appropriate organic substrate which can include catheter tubes, medical tubing introducers, polymer coated medical wires, stents and dilatation balloons by conventional coating application methods. Such methods include dipping, spraying, wiping, painting and the like.

After applying the coating solution, the solvent is preferably allowed to evaporate from the coated substrate often by exposure to ambient conditions of from 2 to 10 minutes. It is preferable to accomplish this evaporation in such a manner as to minimize the accumulation of water in the uncured coating film resulting from hygroscopic attraction of atmospheric moisture to the polyvinylpyrrolidone. This can be accomplished readily by minimizing the evaporation time, reducing the ambient humidity, elevating the ambient temperature for drying, or using a combination of these methods.

The coating is subsequently cured. The cure time and temperatures vary with the choice of isocyanate and polyol and the composition of the substrate. This choice of ingredients also affects the physical properties of the overall coating.

Cure temperatures may range from 75° F. to 350° F. although generally an elevated temperature at 180° to 250° F. is desirable to prevent moisture pickup by the coating during the curing operation. Cure times may vary from 2 minutes to 72 hours, depending upon the reactivity of the isocyanate and polyol, and the cure temperature. In all cases the cure conditions are to be non-deleterious to the underlying substrate.

After the coating is cured, it is preferable to rinse or soak the coating in water to remove any uncomplexed polyvinylpyrrolidone. Generally a brief rinse of 10-15 seconds is sufficient, however a longer rinse or soak is acceptable since the coating is cured and forms a stable gel when in contact with water. After the rinse, the coating may be dried either at ambient conditions, or at elevated temperatures.

After the coating is formed, the coating can imbibe water from an aqueous solution prior to introduction to the body and can become lubricious. Alternatively, the coating can imbibe water solely from body fluids, even if not introduced to water prior to introduction into the body. Because the coating is a cross-linked system, it adheres well to the substrate even when hydrated. It can be dried and remoistened repeatedly and it will retain its lubricating properties. In all cases, the materials are selected so as to be compatible with the body and non-toxic to the body, if the coating is to be used in a body related application as in catheters, introducer tubes and the like.

The organic substrates that can be coated with the coatings of this invention include polyether block amide, polyethylene terephthalate, polyetherurethane, polyesterurethane, other polyurethanes, natural rubber, rubber latex, synthetic rubbers, polyester-polyether copolymers, polycarbonates, and other organic materials. Some of these materials are available under the trademarks such as Pebax available from Atochem, Inc. of Glen Rock, N.J., Mylar available from E. I. duPont deNemours and Co. of Wilmington, Del., Texin 985A from Mobay Corporation of Pittsburgh, Pa., Pellethane available from Dow Chemical of Midland, Mich., and Lexan available from General Electric Company of Pittsfield, Mass.

The polyvinylpyrrolidone of the present invention has a number average molecular weight of from about 50,000 to 2.5 million. PVP having a number average molecular weight of about 360,000 is preferred. Examples of polyvinylpyrrolidone materials useful in this invention are those available from BASF Corp, Parsippany, N.J. as Kollidon 90, Luviskol K90, Luviskol K80 and Luviskol K60, and those available from GAF Corporation, as Plasdone 90, PVP K90 and PVP K120.

Commercially available polyvinylpyrrolidone products usually contain approximately 3-5% (w/w) water. Furthermore, polyvinylpyrrolidone is very hygroscopic, and tends to accumulate water on normal storage when exposed to air. Since water is very reactive toward isocyanates, it is preferred, but not essential, to reduce the water content to less than 0.5% prior to use in preparing coating formulations. This may be readily accomplished by vacuum drying an appropriate quantity of polyvinylpyrrolidone, for example, by heating it for eighteen hours at 200° F. while maintaining a vacuum of 27 inches of mercury.

Isocyanates having at least two unreacted isocyanate groups per molecule may be used and include but are not limited to polymethylenepolyphenyl isocyanate, 4,4'-diphenylmethane diisocyanate and position isomers thereof, 2,4-tolylene diisocyanate and position isomers thereof, 3,4-dichlorophenyl diisocyanate and isophorone isocyanate, adducts or prepolymers of isocyanates and polyols such as the adduct of trimethylolpropane and diphenylmethane diisocyanate or tolylene diisocyanate. Preferably, an adduct or isocyanate prepolymer, such as that available as Vorite 63 from Caschem Inc., is used. For further examples of polyisocyanates useful in this invention see the ICI Polyurethanes Book, George Woods, published by John Wiley And Sons, New York, N.Y. (1987), incorporated herein by reference.

Polyols useful in this invention may be any of a large number of polyols reactive with the isocyanates to form polyurethanes as known in the art. Examples of suitable polyols include but are not limited to, polyester polyols, polyether polyols, modified polyether polyols, polyester ether polyols, castor oil polyols and polyacrylate polyols, including Desmophen A450, Desmophen A365 and Desmophen A160 available from Mobay Corporation of Pittsburgh, Pa. Preferred polyols include castor oil (triglyceride of 12-hydroxy oleic acid) and castor oil derivatives, such as DB 0.1, Polycin-12, Polycin 53 and Polycin 99F all available from Caschem, Inc. of Bayonne, N.J. Suitable diols include poly(ethylene adipates), poly (diethyleneglycol adipates), polycaprolactone diols and polycaprolactone-polyadipate copolymer diols, poly (ethyleneterephthalate) polyols, polycarbonate diols, polytetramethylene ether glycol, ethylene oxide adducts of polyoxypropylene diols, ethylene oxide adducts of polyoxypropylene triols. Many other polyols are available and can be used as known to those skilled in the arts.

The solvents used are those that do not react with the isocyanate, the polyol or the polyvinylpyrrolidone but are solvents for all. The solvents must be free of reactive groups such as, for example, amine, hydroxyl and carboxyl groups. The solvent must further be capable of dissolving the isocyanate, polyol, and polyvinylpyrrolidone. As previously noted, it is preferred that the coating solution be substantially free of water which may react with the isocyanate groups. Thus, it is preferred that the solvent be very dry, that is, that the water content of the solvent used be very low, (e.g., less than 100 ppm). Preferred solvents available commercially in a suitably dry form include but are not limited to methylene chloride, dibromomethane, chloroform, dichloroethane, and dichloroethylene. When methylene chloride is used, the solids content of the coating solution may be 1 to 15% (w/w) and preferably 2.25 to 4% (w/w). When dibromomethane is used, the solids content of the coating solution may be 0.4 to 10% (w/w) and preferably 1.2 to 2.5% (w/w). Other solvents meeting the above objectives are also suitable.

Viscosity and flow control agents may be used to adjust the viscosity and thixotropy to a desired level. Preferably the viscosity is such that the coating can be formed on the substrate at the desired thickness. Viscosities of from 50 cps to 500 cps can be used although higher or lower viscosities may be useful in certain instances. Viscosity control agents include but are not limited to fumed silica, cellulose acetate butyrate and ethyl acrylate/ 2-ethyl hexyl acrylate copolymer. Flow control agents are preferably used in amounts from 0.05 to 5 percent by weight of coating.

Antioxidants are used to improve oxidative stability of the cured coatings and include but are not limited to tris (3,5-di-t-butyl-4-hydroxy benzyl) isocyanurate, 2,2'-methylenebis (4-methyl-6-t-butyl phenol), 1,3,5-Trimethyl-2,4,6-tris (3,5-di-t-butyl-4 -hydroxybenzyl) benzene, butyl hydroxy toluene, octadecyl 3,5, di-t-butyl-4-hydroxyhydrocinnamate, 4,4 methylenebis (2,6-di-t-butylphenol), p,p -dioctyl diphenylamine, 1,1,3-tris-(2-methyl-4-hydroxy-5-t-butylphenyl) butane. Antioxidants are preferably used in amounts from 0.01 to 1 percent by weight of coating.

Conventional pigments can be added to impart color or radiopacity, or to improve appearance of the coatings.

Air release agents or defoamers include but are not limited to polydimethyl siloxanes, 2,4,7,9-tetramethyl-5-decyn-4-7-diol, 2-ethylhexyl alcohol, n-beta-aminoethyl-gamma-aminopropyl-trimethoxysilane. Air release agents are often used in amounts from 0.005 to 0.5 percent by weight of coating.

The invention is further illustrated by the following examples:

EXAMPLE 1

A coating solution of 3% (W/W) total solids was prepared by combining the following ingredients and mixing them thoroughly:
1. 1.09 grams of a toluene diisocyanate—based prepolymer available as Vorite 63 from Cashem, Inc., Bayonne, N.J.
2. 1.16 grams of a castor oil product available as DB oil from Caschem, Inc.
3. 150 grams of a 5% (w/W) solution of polyvinylpyrrolidone, PVP K-90, available as Kollidon 90 from BASF Inc., Wyandotte, Mich., in methylene chloride. Prior to preparing this solution, the Kollidon 90 was vacuum dried for 18 hours at 200° F., under an approximate 27" Hg vacuum.
4. 173 grams of methylene chloride.

The resulting solution contained 30 parts by weight of polyurethane precursors (isocyanate and polyol, collectively) to 100 parts PVP.

A 10" length of polyurethane catheter tubing was coated with the resulting solution by dipping during 20 seconds. The solvent was evaporated at room temperature for approximately 5 minutes. The tubing was then placed in an oven at 225° F. for 120 minutes to effect cure of the coating.

Upon removal from the oven, the tubing was rinsed in water and dried.

The result was an adherent thin, tough coating on the tubing which, when wetted with water, becomes an extremely slippery hydrogel. When wet, the coating maintained a high degree of lubricity even after rubbing 20 times with firm finger pressure applied under a stream of running water. The coating was allowed to dry. Upon re-wetting, the lubricity was unchanged. The drying and re-wetting cycles were repeated 10 times with no loss of lubricity.

A similar length of coated tubing was stored in water at room temperature for a period of 10 days. After 10 days it exhibited essentially the same degree of lubricity and durability as described above.

The coating solution was stored in a clean, tightly capped glass container for 28 days. After 28 days, a length of polyurethane tubing was coated and processed as described above. The resulting coating performed essentially the same as described above, demonstrating a useful pot life of at least 28 days for this formulation.

EXAMPLE 2

A coating solution of 3% (w/w) total solids was prepared by combining the following ingredients and mixing them thoroughly:
1. 1.82 grams of Vorite 63.
2. 1.94 grams of D.B. oil.
3. 300 grams of a 5% (w/w) solution of Kollidon 90 in methylene chloride.
4. 320 grams of methylene chloride.

The resulting solution contained 25 parts by weight of polyurethane precursors to 100 parts PVP.

A 10" length of polyurethane catheter tubing was coated with this solution by dipping during 20 seconds. The solvent was evaporated at room temperature for approximately 5 minutes. The tubing was then placed in an oven at 225° F. for 120 minutes to effect a cure.

The tubing was then rinsed after removal from the oven, and dried.

The result was a coating with properties which were essentially identical to those described in Example 1.

The coating solution was stored for 23 days as described in Example 1, after which a length of polyurethane tubing was coated and processed as described above. The resulting coating was essentially identical to that described in Example 1, demonstrating a useful pot life of at least 23 days.

EXAMPLE 3

A coating solution of 1.8% (w/w) total solids was prepared by combining the following ingredients and mixing them thoroughly:
1. 1.50 grams of Vorite 63.
2. 1.62 grams of DB oil.
3. 260 grams of a 3% (w/w) solution of Kollidon 90 in dibromomethane.
4. 342 grams of dibromomethane.

The resulting solution contained 40 parts by weight of urethane precursors to 100 parts PVP K90.

A 12" length of catheter tubing made of polyether-block amide polymer, available as Pebax 4033, from Atochem, Inc., Glen Rock, N.J., was coated with this solution as in Example 1.

The result was a lubricious, adherent coating essentially identical to that described in Example 1.

The solution was stored for 5 days, and a second length of polyether block amide tubing was similarly coated, with essentially the same results, indicating a useful pot life of at least 5 days.

EXAMPLE 4

A coating solution of 2.8% (w/w) total solids was prepared by combining the following ingredients and mixing them thoroughly:
1. 60 grams of Vorite 63.
2. 1.70 grams of DB oil.
3. 200 grams of a 3% (w/w) solution of polyvinylpyrrolidone, K-120, available as Plasdone K-120 from GAF Corp., Wayne, J. J. and which was first vacuum dried as in Example 1, in methylene chloride.
4. 129 grams of methylene chloride.

The resulting solution contained 55 parts by weight of polyurethane precursors to 100 parts of PVP K120.

A 10" length of polyurethane catheter tubing was coated with this solution and processed as described in Example 1.

The resulting coating was very lubricious, with essentially the same properties as those described in Example 1.

COMPARATIVE EXAMPLE 5

A coating solution of 3% (w/w) total solids was prepared by combining the following ingredients and mixing them thoroughly:
1. 1.86 grams of Vorite 63.
2. 1.14 grams of a polyethylene glycol of average molecular weight of 400, available as CARBOWAX PEG 400 from Union Carbide Corp., of Danbury Conn.
3. 150 grams of a 5% (w/w) solution of Kollidon 90 in methylene chloride.
4. 197 grams of methylene chloride.

The resulting solution contained 40 parts by weight of polyurethane precursors to 100 parts PVP K90.

A 10" length of polyurethane catheter tubing was coated with this solution and processed as described in Example 1.

Importantly, this is an example of the formation of an essentially linear, instead of a crosslinked, polyurethane, since both the isocyanate prepolymer and the polyol have a functionality of 2.

The resulting coating was wetted with water and tested for lubricity. It was initially very slippery, but after rubbing 10 times with firm finger pressure under a stream of running water, the coating was largely removed, as evidenced by a dramatic decrease in lubricity. The presence of removed coating could also be detected between the fingers during this evaluation.

Evidently a linear polyurethane formed in place during the cure of the coating does not produce a gel of sufficient integrity to withstand a practical degree of abrasion.

COMPARATIVE EXAMPLE 6

A coating solution of 3% (w/w) total solids was prepared by combining the following ingredients and mixing them thoroughly:
1. 40 grams of a 5% (w/w) solution of a linear polyetherurethane, available as Estane 5703, from B. F. Goodrich Co., of Cleveland, Ohio, in methylene chloride.
2. 100 grams of 5% (w/w) solution of Kollidon 90 in methylene chloride.
3. 93 grams of methylene chloride.

The resulting solution contained 40 parts of linear, preformed polyurethane to 100 parts of PVP K90. NOTE: This is an example of a linear, instead of a crosslinked, polyurethane in combination with PVP.

A 10" length of polyurethane catheter tubing was coated with this solution and processed as described in Example 1.

The resulting coating was wetted with water and tested, with results essentially the same as in comparative Example 5. That is, the wetted coating displayed initial integrity, but began to lose lubricity and show evidence of coating wear after 10 finger rubs under running water.

COMPARATIVE EXAMPLE 7

In an attempt to produce a coating similar to the one described in COMPARATIVE EXAMPLE 6 but with improved durability, a coating solution with a higher ratio of polyurethane to PVP was prepared as a 3% (w/w) solution by combining the following ingredients and mixing thoroughly.
1. 50 grams of a 5% (w/w) solution of Estane 5703 in methylene chloride.
2. 50 grams of a 5% (w/w) solution of Kollidon 90 in methylene chloride.

The resulting solution contained 100 parts of linear, preformed polyurethane to 100 parts of PVP K90.

A 10" length of polyurethane catheter tubing dipped in this solution and processed as described previously was then wetted with water and tested. The coating, although more durable, was found to display very little lubricity.

COMPARATIVE EXAMPLE 8

A coating solution of 3% (w/w) was prepared by combining the following ingredients and mixing thoroughly.
1. 3.0 grams of Vorite 63.
2. 150 grams of a 5% (w/w) solution of Kollidon 90 in methylene chloride.
3. 197 grams of methylene chloride.

The resulting solution contained 40 parts of Vorite 63 to 100 parts of PVP K90. Importantly, this is an example of a blend of an isocyanate prepolymer and PVP K90. Since no polyol is present, the formation of a crosslinked polyurethane is not possible.

A 10" length of polyurethane catheter tubing dipped in this solution and processed as described previously was then wetted with water and tested. The results were essentially the same as in COMPARATIVE EXAMPLE 5, that is lubricious at first, but losing lubricity and showing evidence of coating loss after 20 finger rubs under running water. Presumably, the poor durability was due to the inability of the isocyanate to form a crosslinked polyurethane network, because of the lack of a polyol species.

EXAMPLE 9

A coating solution of 3% (w/w) total solids was prepared by combining the following ingredients and mixing them thoroughly:
1. 1.96 grams of Vorite 63

2. 1.04 grams of a modified castor oil based polyol of approximate functionally of 4 available as Polycin 12 from Caschem, Inc.
3. 150 grams of a 5% (w/w) solution of Kollidon 90 which was first vacuum dried as in Example 1, in methylene chloride.
4. 197 grams of methylene chloride.

The resulting solution contained 40 parts of polyurethane precursors to 100 parts PVP K90.

A 10" length of polyurethane catheter tubing was dip coated in this solution and processed as described in Example 1.

The result was a coating with properties that were essentially identical to those described in Example 1.

EXAMPLE 10

A coating solution of 2.75% (w/w) was prepared by combining the following ingredients and mixing them thoroughly:
1. 1.45 grams of Vorite 63.
2. 1.55 grams of DB oil.
3. 150 grams of a 5% (w/w) solution of Kollidon 90 which was first vacuum dried as in Example 1, in methylene chloride.
4. 229 grams of methylene chloride.

The resulting solution contained 40 parts of polyurethane precursors to 100 parts of PVP K90.

10" lengths of the following types of tubing were dip coated in this solution and processed as described in Example 1.
a. Latex tubing
b. Polyesterurethane tubing made from Estane, 58206, available from B. F. Goodrich Co., Cleveland Ohio.
c. Polyetherurethane tubing made from Estane, 58300, available from B. F. Goodrich.

In all cases the result was a durable very slippery coating when wet, similar to that described in Example 1.

EXAMPLE 11

A coating solution of 3% (w/w) was prepared by combining the following ingredients and mixing them thoroughly:
1. 1.33 grams of a 60% solution of the adduct of toluene diisocyanate and trimethylolpropane in methoxy acetoxy propane (available as Mondur CB-60 PMA from Mobay Corporation, Pittsburgh, Pa.;
2. 1.60 grams of Vorite 63;
3. 1.37 grams of Polycin 12;
4. 200 grams of a 5% (w/w) solution of Kollidon 90 which was first vacuum dried as in Example 1, in methylene chloride.
5. 247 grams of methylene chloride.

The resulting solution contained 35 parts of polyurethane precursors to 100 parts PVP K90. 10" lengths of the following types of tubing were dip coated in this solution and processed as described in Example 1.
a. Latex tubing.
b. Polyesteruethane tubing made from Estane 58206.
c. Polyetherurethane tubing made from Estane 58300.
In all cases the result was a durable, very slippery coating when wet, similar to that described in Example 1.

EXAMPLE 12

A coating solution of 1.8% (w/w) was prepared by combining the following ingredients and mixing them thoroughly:
1. 1.26 grams of Vorite 63;
2. 1.14 grams of DB oil;
3. 0.84 grams of a 1% solution of a hindered phenol antioxidant (available as Irganox 1076 from Ciba Geigy Corp., Ardsley N.Y.) in methylene chloride;
4. 200 grams of a 3% (w/w) solution of Kollidon 90 which was first vacuum dried as in Example 1, in dibromomethane.
5. 264 grams of dibromethane.

The resulting solution contained 40 parts of polyurethane precursors to 100 parts PVP.

A ureteral stent formed from a polyesterurethane was dip coated in this solution for 8 seconds. The solvent was evaporated at room temperature for approximately 15 minutes. The stent was placed in an oven at 225° F. for 120 minutes to effect cure of the coating.

Upon removal from the oven, the stent was rinsed in water and dried.

The result was a durable, slippery coating when wet, similar to that described in Example 1.

The stent was tested for coefficient of friction following ASTM D1894-87 and demonstrated a value of 0.02. By comparison, a similar size of latex tubing coated with polytetrafluoroethylene (available as Teflon from E. I. du Pont de Nemours, Wilmington, Del.) exhibited a coefficient of friction value of 0.40.

EXAMPLE 13

A coating solution of 3% (w/w) was prepared by combining the following ingredients and mixing them thoroughly.
1. 2.56 grams of Vorite 63;
2. 7.44 grams of a saturated polyester polyol (available as Multron R-18 from Mobay Corp.);
3. 200 grams of a 5% (w/w) solution of Plasdone K90 which was first vacuum dried as in Example 1, in methylene chloride.
4. 456 grams of methylene chloride.

The resulting solution contained 100 parts of polyurethane precursors to 100 parts of PVP K90.

A clean latex rubber urological catheter with a chlorinated surface was dip coated in this solution for 45 seconds. The solvent was evaporated at room temperature for approximately 10 minutes. The catheter was then placed in an oven at 225° F. for 120 minutes to effect cure of the coating.

Upon removal from the oven, the catheter was rinsed in water and dried.

The result was a catheter with a durable and extremely lubricious coating when wet.

EXAMPLE 14

A coating solution of 2.5% (w/w) total solids was prepared by combining the following ingredients and mixing them thoroughly:
1. 2.98 grams of Mondur CB-60 PMA;
2. 1.03 grams of CARBOWAX PEG 400;
3. 1.40 grams of a 1% solution of Irganox 1076 in methylene chloride;
4. 200 grams of a 5% (w/w) solution of Kollidon 90 which was first vacuum dried as in Example 1, in methylene chloride.
5. 307 grams of methylene chloride.

The resulting solution contained 40 parts of polyurethane precursors to 100 parts of PVP K90.

10" lengths of latex tubing were dip coated in this solution during 30 seconds, and solvent was evaporated for approximately 15 minutes. The tubing was then placed in an oven at 200° F. for 1 hour to effect cure of the coating.

Upon removal from the oven, the tubing was rinsed briefly with water and dried. NOTE: This is an example of a crosslinked polyurethane produced by the reaction of a tri-functional isocyanate (Mondur CB-60 PMA) with a difunctional polyol (CARBOWAX PEG 400).

The result was a thin, tough, adherent coating which becomes extremely slippery when wetted with water. The coating could not be removed with repeated firm finger pressure applied under a stream of running water, and maintained lubricity after such rubbing.

A length of tubing was tested for coefficient of friction per ASTM D1894-87 in a water bath at 100° F. A coefficient of friction value of 0.02 was measured. By comparison, a similar length of latex tubing coated with polytetrafluoroethylene (Teflon, available from E. I. du Pont de Nemours and Co., Wilmington, Del.) exhibited a coefficient of friction value of 0.40.

While the invention has been described in detail and with reference to specific embodiments thereof, it will be apparent that various changes and modifications can be made therein without departing from the spirit and scope thereof.

What is claimed is:

1. An article comprising a substrate on which is coated a hydrophilic, lubricious, organic coating comprising a crosslinked polyurethane and a polyvinylpyrrolidone, said crosslinked polyurethane formed from the reaction of an isocyanate and a polyol, said isocyanate containing at least two NCO groups per molecule and the polyol having at least two hydroxy groups per molecule, the sum of the average NCO functionality and the average hydroxy functionality exceeding 4.

2. An article comprising a substrate on which is coated a coating in accordance with claim 1 wherein the polyvinylpyrrolidone has a number average molecular weight of from about 50,000 to 2.5 million.

3. An article comprising a substrate on which is coated a coating in accordance with claim 2 wherein the polyvinylpyrrolidone has a number average molecular weight of about 360,000.

4. An article comprising a substrate on which is coated a coating in accordance with claim 1 wherein the ratio by weight of the polyurethane to polyvinylpyrrolidone is from about 0.05 to 3.0.

5. An article comprising a substrate on which is coated a coating in accordance with claim 4 wherein the ratio by weight is from about 0.2 to 1.0.

6. An article comprising a substrate on which is coated a coating in accordance with claim 1 wherein the crosslinked polyurethane is formed in the presence of polyvinylpyrrolidone.

7. An article comprising a substrate on which is coated a coating in accordance with claim 1 wherein the stoichiometric ratio of total NCO groups to total hydroxy groups is from about 0.75 to 3.0.

8. An article comprising a substrate on which is coated a coating in accordance with claim 7 wherein the stoichiometric ratio of total NCO groups to total hydroxy groups is from about 1.1 to 1.3.

9. An organic substrate article having a hydrophilic coating comprising:
   an organic substrate,
   and the coating in accordance with claim 1 adhered thereto.

10. The article of claim 9 wherein the organic substrate is of a material selected from the group consisting of polyether block amides, polyurethanes, polyetherurethanes, polyester urethanes, natural rubber, synthetic rubber, latex rubber, polyester-polyether copolymers, polycarbonates and polyethylene terephthalates.

11. An article comprising an organic substrate and a hydrophilic, lubricious organic coating adhered thereto, said coating formed from the reaction on the surface of the substrate to be coated, of a mixture comprising an isocyanate, a polyol and polyvinylpyrrolidone in a carrier liquid to form a crosslinked polyurethane-polyvinylpyrrolidone coating, said isocyanate containing at least two NCO groups per molecule and the polyol having at least two hydroxy groups per molecule, the sum of the average NCO functionality and the average hydroxy functionality exceeding 4.

12. An article in accordance with claim 11 wherein the polyvinylpyrrolidone has a mean molecular weight of from about 50,000 to 2.5 million.

13. An article in accordance with claim 12 wherein the mixture contains a blend of polyvinylpyrrolidones.

14. An article in accordance with claim 11 wherein the isocyanate has at least two unreacted isocyanate groups per molecule and is selected from the group consisting of 2,4- and 2,6 Toluene Diisocyanate (TDI), 4,4'- diphenylmethonediisocyanate (MDI), other position isomers of MDI, polymeric versions of MDI, hexamethylene diisocyanate, and adducts and prepolymers prepared from the above.

15. An article in accordance with claim 11 wherein the polyol used is selected from the group consisting of castor oil and castor oil derivatives, modified polyether polyols, modified polyester polyols, and polyethylene glycols.

16. An article in accordance with claim 11 wherein the carrier liquid is a solvent selected from the group consisting of methylene chloride, dibromomethane, chloroform, dichloroethane, acetonitrile, dibromoethane and blends thereof.

* * * * *